US00PP13850P39

(12) United States Plant Patent
Hirabayashi

(10) Patent No.: US PP13,850 P3
(45) Date of Patent: May 27, 2003

(54) PETUNIA PLANT NAMED 'KEIDOPUEL'

(75) Inventor: Hiroshi Hirabayashi, deceased, late of Yachiyo (JP), by Eriko Hirabayashi, Minako Hirabayashi, Kanako Hirabayashi, heirs

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/929,155

(22) Filed: Aug. 13, 2001

(65) Prior Publication Data

US 2003/0033654 P1 Feb. 13, 2003

(51) Int. Cl.[7] ..... A01H 5/00

(52) U.S. Cl. ..... Plt./356

(58) Field of Search ..... Plt./356

(56) References Cited

PUBLICATIONS

UPOV–ROM GTITM Computer Database, 2001/06, GTI Jouve Retrieval Software, citation for 'Keidopuel'.*

* cited by examiner

*Primary Examiner*—Bruce R. Campell
*Assistant Examiner*—Susan B. McCormick
(74) *Attorney, Agent, or Firm*—Klarquist Sparkman, LLP

(57) ABSTRACT

Petunia plant having a vivid purple coloration.

2 Drawing Sheets

Genus and Species

*Petunia hybrida.*

Variety Denomination

KEldopuel.

SUMMARY OF THE INVENTION

The present invention relates to a new and distinct variety of Petunia which was originated by me by crossing two unnamed seedlings, each of whose parents were also unnamed seedlings, none of which are patented.

BACKGROUND OF THE INVENTION

The primary objective of this breeding was to produce a new Petunia variety having large flowers of a vivid purple color and a plant having a strong growth habit. The objective was substantially achieved

BRIEF SUMMARY OF THE INVENTION

The objective was substantially achieved, along with other desirable improvements as evidenced by its unique combination of characteristics that are outstanding in the new variety and distinguish it from its parents as well as from all other varieties of which I am aware.

Asexual reproduction of this new variety by cuttings, as performed at Yachigo-shi, Chiba-Ken, Japan and at Somis, Calif., shows that the foregoing and all other characteristics and distinctions come true to form and are established and transmitted through succeeding propagations.

COMPARISON WITH SIMILAR VARIETY

As compared to the Petunia variety KERpril, KEIdopuel's flower is larger and the plant has a stronger growth habit.

BRIEF DESCRIPTION OF THE ILLUSTRATIONS

The accompanying illustrations show a typical specimen of this new variety, depicted in color as nearly true as it is reasonably possible to make the same in a color illustration of this character:

DETAILED BOTANICAL DESCRIPTION

Figure 1:
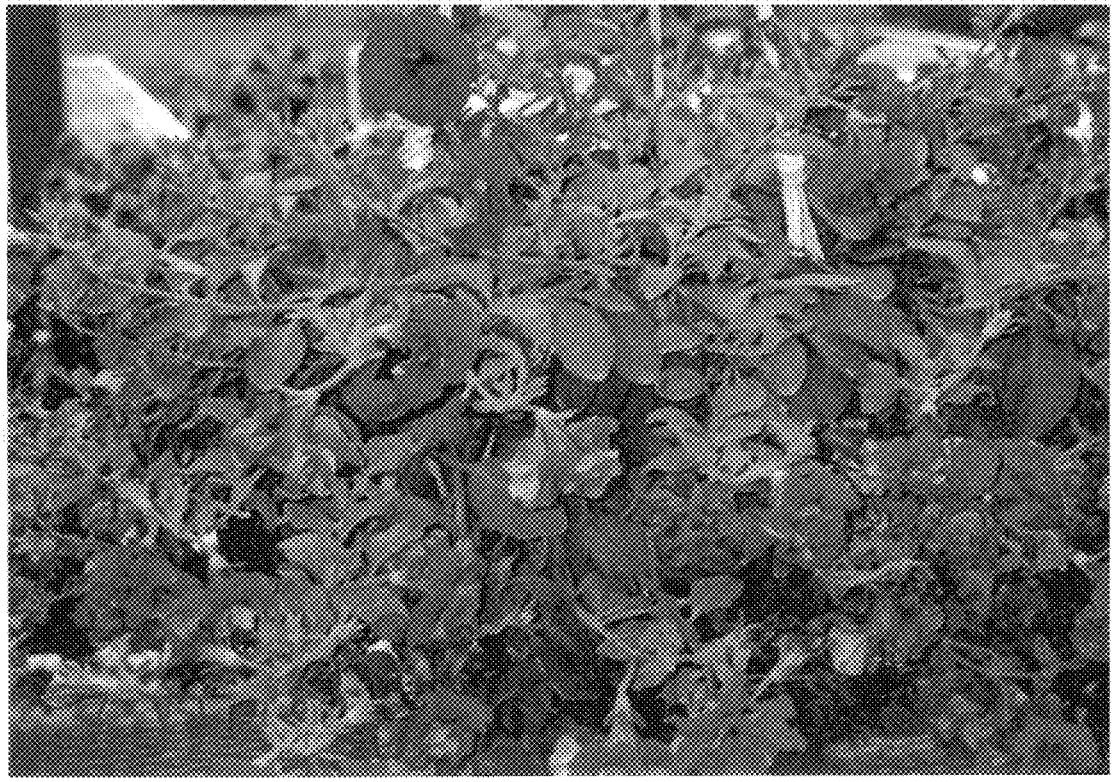
FIG. 1 is a photograph of a portion of a mature plant.
Figure 2:
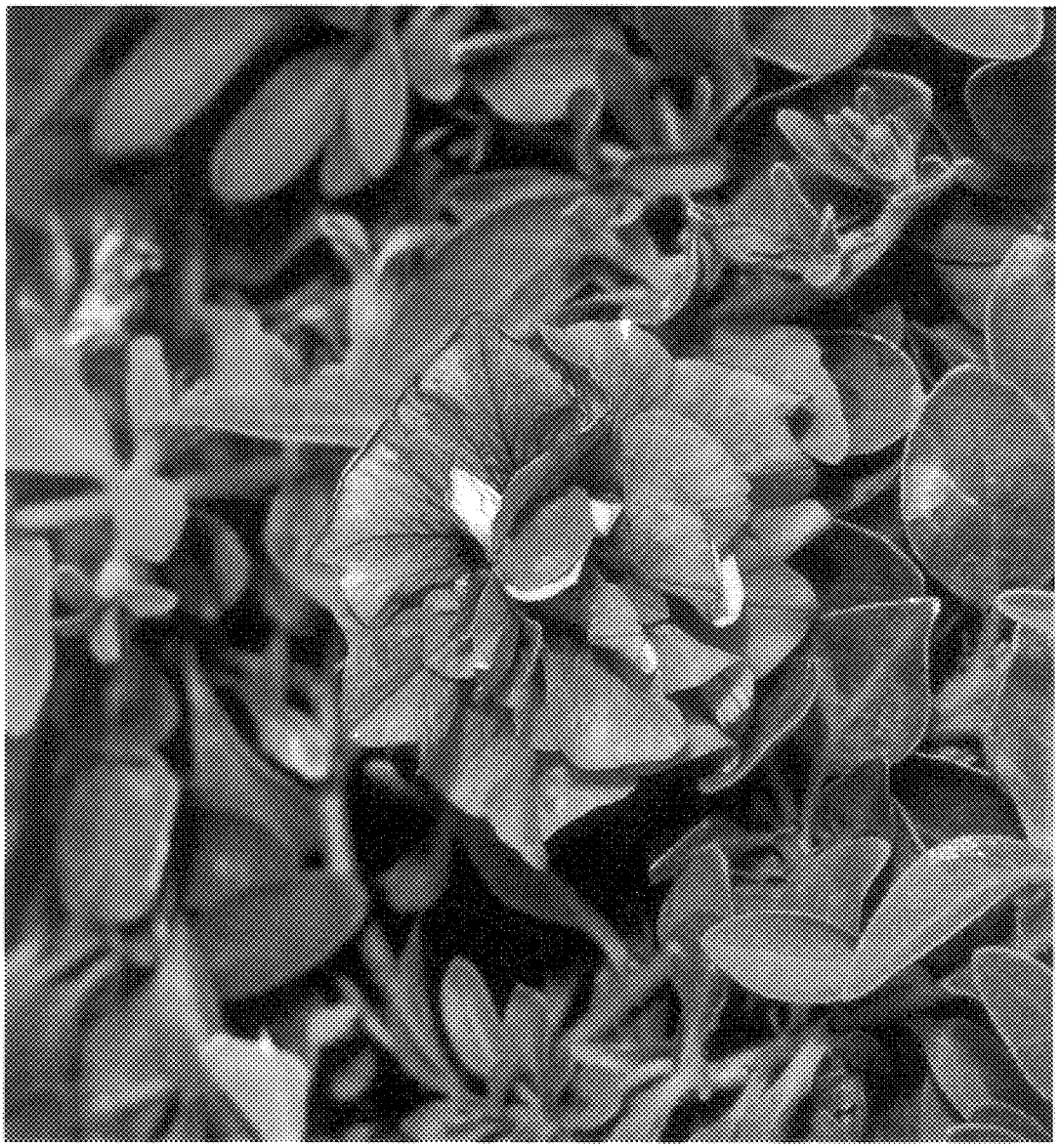
FIG. 2 is an enlarged view of a single blossom as it appears on the plant.

The following is a detailed description of my new petunia cultivar with color descriptions using terminology in accordance with The Royal Horticultural Society (London) Colour Chart, except where ordinary dictionary significance of color is indicated.

Parentage:

*Seed parent.*—Unnamed seedling (unpatented).
*Pollen parent.*—Unnamed seedling (unpatented).

Observations made from specimens beginning at three months of age grown in a garden environment at Somis, Calif. from July, 2000 to December, 2000.

Plant:

*Growth.*—Spreading.
*Growth habit.*—Vigorous, free branching.
*Rooting time.*—About two weeks.
*Mature plant.*—Height: 10–15 cm. Spreading area: 30–40 cm in diameter.
*Blooming period.*—April to October.
*Stem.*—Overall Length 11–20 cm. Main Stem: about 20 cm. Laterals: 11–15 cm. Thickness: 2.0–2.5 mm. Color: Yellow-Green Group 146B. Pubescence: Pubescent. Mode of branching: Abundant Length of internode: 3–4.5 cm.

*Leaf.*—Arrangement on stem: Slantly upward. Shape: Elliptic. Base shape: Acute. Apex shape: Acute. Size: Width: 3.5 cm; Length 5.0 cm. Thickness: About 1 mm. Color: Upper surface: Yellow-Green Group 146A. Lower surface: Yellow-Green Group 146A. Phyllotaxis: Perpendicular. Pubescence: Pubescent. Venation pattern: Pinnate. Vein Color: Yellow-Green Group 146A.

Flower:

*Size.*—2¾–3¼ inches in diameter.

*Type.*—Double.

*Shape.*—Corolla wheel-shaped with a short tube and wide, horizontally flowing limbs.

*Color.*—The upper sides of the petals are vivid Red-Purple Group 74A. The reverse sides of the petals are Purple Group 76C at the time of petal opening but changing as the petal ages progressively to Purple Group 76B, Purple Group 75C, Red-Purple Group 73C and finally to Red-Purple Group 68D before petal shrivels.

*Peduncle.*—Length: 1.5–2.5 cm. Diameter: 0.25 cm. Color: Yellow-Green Group 146C.

*Calyx.*—Number of sepals: 5. Length: 11–13 mm. Color: Yellow-Green Group 146C.

*Corolla.*—Length: 4.1 cm. Diameter: 5.2 mm. Color: Red-Purple Group 74A.

Reproductive parts:

*Anthers.*—Color: Violet Group 84C and 84D.

*Filaments.*—Color: Yellow-Green Group 150D.

*Pistil.*—Quantity: One. Color: Greyed-Yellow Group 160D.

*Stamens.*—Quantity: 3–5.

*Fruit.*—None observed.

Disease resistance: Resistant to mildew under normal growing conditions.

Response to climatic conditions: Hardy to Zone 10.

It is claimed:

1. A new and distinct variety of Petunia plant, substantially as herein shown and described, characterized particularly by its vivid purple coloration.

* * * * *

UNITED STATES PATENT AND TRADEMARK OFFICE

CERTIFICATE OF CORRECTION

PATENT NO. : PP 13,850 P3
DATED : May 27, 2003
INVENTOR(S) : Hirabayashi

It is certified that error appears in the above-identified patent and that said Letters Patent is hereby corrected as shown below:

Column 1,
Line 6, "KEldopuel" should be -- KEIdopuel --.

Signed and Sealed this

Twentieth Day of January, 2004

JON W. DUDAS
*Acting Director of the United States Patent and Trademark Office*